United States Patent [19]

Schmidtpott et al.

[11] Patent Number: 4,816,749
[45] Date of Patent: Mar. 28, 1989

[54] ELECTROCEMICAL SENSOR

[75] Inventors: Hermann Schmidtpott, Germering; Ingeborg Wagner, Munich, both of Fed. Rep. of Germany

[73] Assignee: Bayer Diagnostic & Electronic GmbH, Munich, Fed. Rep. of Germany

[21] Appl. No.: 3,428

[22] PCT Filed: Apr. 15, 1986

[86] PCT No.: PCT/EP86/00217
§ 371 Date: Feb. 9, 1987
§ 102(e) Date: Feb. 9, 1987

[87] PCT Pub. No.: WO86/06168
PCT Pub. Date: Oct. 23, 1986

[30] Foreign Application Priority Data

Apr. 17, 1985 [DE] Fed. Rep. of Germany ....... 3513761

[51] Int. Cl.[4] ............................................. G01N 27/00
[52] U.S. Cl. ..................................... 324/711; 204/427; 324/425
[58] Field of Search ..................... 324/71.1, 71.5, 425; 73/23; 340/634; 204/424, 426, 427, 428

[56] References Cited

U.S. PATENT DOCUMENTS

| | | | |
|---|---|---|---|
| 3,738,341 | 6/1973 | Loos | 324/425 |
| 4,394,239 | 7/1983 | Kitzelmann et al. | 204/414 |
| 4,437,971 | 3/1984 | Csanitz et al. | 204/427 |
| 4,502,939 | 3/1985 | Holfelder et al. | 204/427 X |
| 4,638,443 | 1/1987 | Kaneyasu et al. | 340/634 X |

*Primary Examiner*—Reinhard J. Eisenzopf
*Assistant Examiner*—Robert W. Mueller
*Attorney, Agent, or Firm*—Sprung Horn Kramer & Woods

[57] ABSTRACT

The electrochemical sensor, which is designed more especially for monitoring the correct function of exhaust gas cleaning means in exhaust gas systems, has a solid electrolyte and a diffusion barrier of porous material and is arranged downstream from the exhaust gas cleaning means in the exhaust gas pipe. The sensor operates in a temperature range of $-50°$ C. to $500°$ C., throughout which it functions substantially independently of temperature. Preferably nitrogen oxides are used as representative components for monitoring the efficacy of the exhaust gas cleaning means and a signal is produced when the signal from the sensor exceeds a given value.

19 Claims, 1 Drawing Sheet

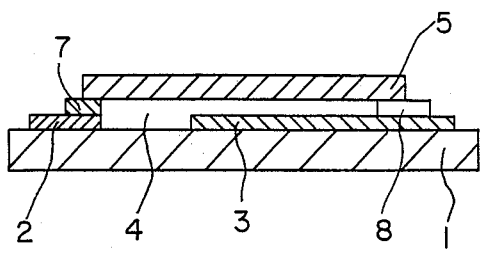
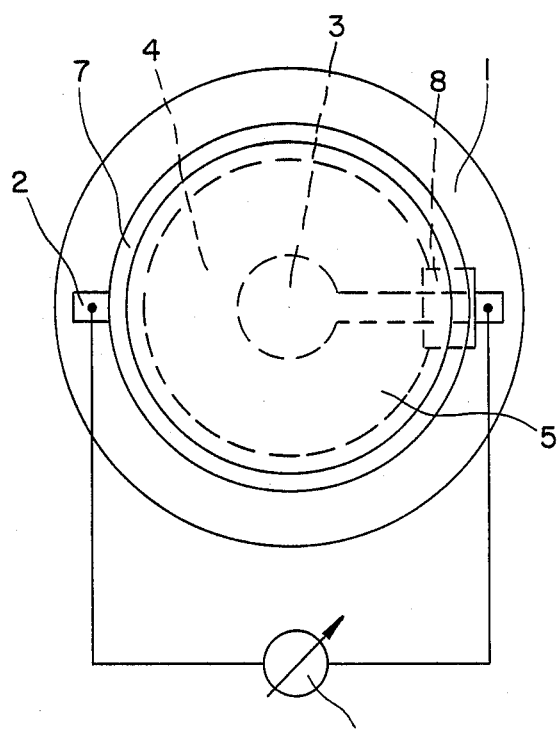

ELECTROCEMICAL SENSOR

BACKGROUND OF THE INVENTION

The invention relates to an electrochemical sensor for the detection of nitrogen oxides.

The German unexamined specification No. 2,304,464 describes a sensor for monitoring the function of catalysts in the exhaust gas cleaning systems of internal combustion engines. The sensor consists of an oxygen or λ probe. If the catalyst is poisoned or if for some other reason, such as aging, the catalyst is not capable of functioning fully to oxidize or reduce, respectively, hydrocarbons, carbon monoxide, or nitrogen oxides, a higher oxygen concentration will appear downstream for the catalyst, since the oxygen will then not be consumed catalytically. In the said known arrangement the sensor is arranged downstream from the catalyst and measures the oxygen coming from the catalyst. On reaching a certain, preset value, a signal is then produced which indicates that the catalyst is no longer, or no longer sufficiently, active.

The ability of a catalyst to convert hydrocarbons, carbon monoxide and oxides of nitrogen into less harmful gases by oxidation is not ascertained directly in the known device, but rather indirectly by measuring the oxygen still appearing downstream from the catalyst. This method is very inaccurate and is unsuitable for practical application, since the oxygen concentration downstream from the catalyst is not only dependent on the function of the catalyst by itself but furthermore on the manner of operation of the engine in the various load ranges. Moreover the measurement of the oxygen concentration downstream from the catalyst may not be used for evaluating the function of the catalyst, because such data do not represent the nitrogen oxide concentration downstream from the catalyst. Accordingly, the known device is not able to reliably monitor the function of a catalyst.

The German unexamined specification No. 2,335,402 describes a sensor for the electrochemical determination of the content of nitrogen oxides in exhaust gases, which amongst other things is used to monitor the function of an exhaust gas catalyst. Such a sensor is arranged in an exhaust pipe shunt and the maximum permitted temperature of the known sensor is 70° C. owing to its design and for instance owing to the use of Teflon as a diffusion barrier.

The disadvantage of this device is more especially that the nitrogen oxide fraction in the exhaust gas is not measured downstream from the catalyst but in the shunt or bypass. Downstream from the catalyst there is a temperature of at least 400 degrees in the exhaust system, i. e. in the exhaust gas. The known sensor is in no way able to withstand this temperature. Accordingly the sensor in the shunt in addition has to be cooled, something creating added complexity. It is furthermore possible for the shunt to be shut off intentionally or unintentionally and as a result no reliable monitoring of the catalyst will be possible.

Although there are methods of physical analysis by which nitrogen oxides, hydrocarbons and/or carbon monoxide may be measured at temperatures of 400° C., flame ionisation detectors, infrared analyzers and/or chemoluminescence measuring instruments are used for this purpose, which without exception represent complicated items of apparatus and are in no way suitable for use in exhaust systems both on account of the expense and also as regards the amount of space required, mechanical stability and other factors.

SUMMARY OF THE INVENTION

Accordingly the object of the invention is to devise an electrochemical sensor, and more particularly a sensor for nitrogen oxides as representative components of exhaust gases, and also for carbon monoxide and/or hydrocarbons, which operates satisfactorily even at maximum temperatures, which both as regards its dimensions and also as regards mechanical stability, that is to say compactness and resistance to vibrations, is suitable for incorporation in motor vehicles, may be produced at a low price, operates reliably in a temperature range of approximately −50° C. to +500° C. and is essentially independent of the engine load and the degree of combustion therein.

This object is attained by arranging the sensor in the exhaust duct on the output side of the catalyst relative to the flow of the gas and providing a solid electrolyte and a diffusion barrier of a porous metal.

Owing to the fact that in the electrochemical sensor of the present invention there is a solid electrolyte and the diffusion barrier consists of porous metal, and owing to the possibility of arranging the sensor downstream from the catalyst in the exhaust pipe, there is reliable determination of an exhaust gas component not reacted by the catalyst. The representative component is normally the nitrogen oxides, but by using the sensor in accordance with the invention it is also however possible to determine the amount of hydrocarbons or the carbon monoxide in order to assure a reliable monitoring of the function of the catalyst. The result is then a continuous monitoring of the catalyst, which is more particularly independent of the amount of oxygen in the exhaust gases. Furthermore, the determination of the exhaust gas component is generally not dependent on the varying load of the engine, which changes in rapid succession, as for instance on speeding up starting from idling, then overtaking, or if when on a highway the engine has to develop full power.

More particularly the sensor in accordance with the invention is mechanically very robust, as is necessary either in a motor vehicle exhaust gas system, owing to the vibration of the vehicle and pulsations in the exhaust gas, or indeed in exhaust gas systems for stationary plant. Moreover, sensors in accordance with the invention are simple in structure and manner of manufacture and accordingly are low in price. A further advantage of the sensors in keeping with the invention is that they are not able to be poisoned by water vapor and gasoline. If a sensor in keeping with the invention is employed for the determination of the amount of nitrogen oxides, it will not have any cross-sensitivity or induced sensitivity to carbon monoxide, carbon dioxide, sulfur oxides or hydrogen.

In keeping with a preferred form of the present invention the diffusion barrier is constructed in the form of a porous layer of the material forming the operating electrode. This is useful inasfar as the adhesion, by way of a solid layer of the same material, of the porous layer on the substrate, as for instance a ceramic plate or a suitably pre-treated metal plate, is substantially superior to the adhesion of the porous layer directly on the substrate.

Furthermore the connection of the electrical lead is simpler and more secure.

It is preferably possible for the diffusion barrier consisting of porous material to be able to function as the operating electrode. The gas molecules passing through the diffusion barrier with a definite volume interact with the electrochemical system in the three phase space thereof.

In accordance with the specific conditions, requirements and the selection of the materials, electrolyte etc., it is also possible to provide an additional reference electrode. In this case the operating and counter electrode, that is to say the cathode and the anode may be made of the same material. If in a further possible, alternative form of the invention, the counter electrode simultaneously serves as a reference electrode, then the counter electrode will be made of a material different to that of the operating electrode.

The solid electrolyte is preferably a compound or a mixture of compounds, which throughout the working temperature range of −50° C. to +500° C. will have a conductivity of at least 10–11 ohm/cm in order to ensure that the output signal of the sensor is large enough for further processing.

Preferably compounds or mixtures of compounds are utilized which do not undergo any change in phase and more particularly do not undergo any change in the crystalline phase and do not decompose in the said operating temperature range. This is to ensure the thermal stability of the solid electrolyte throughout the temperature range.

Particularly advantageous solid electrolytes are spinels, more especially suitable members of this group of compounds being zirconium phosphate, khibinskite, wadeites, titisicon, nasicon, stibic acid and uranyl arsenide.

Further particularly suitable materials for use as solid electrolytes are heteropolyacids, as for example hydrogen uranyl phosphate, tungstatophsophoric acid and molybdatophosphoric acid. The spinels and heteropolyacids are more particularly suitable on account of their thermal stability and their constant conductivity over a large temperature range.

As regards the selection of the material for the solid electrolyte it is preferred to use one which is essentially inert with respect to the electrode material so that the working life of sensors may be extended.

The operating electrode is preferably made of gold and the diffusion barrier is peferrably made of porous gold. In certain circumstances it is possible to utililize other materials for the operating electrode.

The counter electrode consists of at least one of the materials from the group of platinum, palladium, rhodium, silver and ruthenium oxide, same being more particularly advantageous.

In the event of an additional reference electrode being employed, it is particularly expedient if it is made of $AgNO_3$ with a counter electrode of silver. If a two electrode system is used in which the counter electrode is simultaneously the reference electrode, it is furthermore particularly advantageous if the latter is formed from at least one of the mixtures including Pd/PdO, Ni/NiO, Cu/$Cu_2$O, Ag/AgCl and Pd/$PdH_x$. Such electrodes have a particularly low polarisibility and maintain a sufficiently constant potential even when a current is flowing. The essential criterion for the selection of such systems is that they should operate reversibly in the respective temperature range. In the event of mixtures of oxides having a high electrical conductivity, they may also be used for the electrodes, despite a small phase width.

The sensors in keeping with the invention have a high selectivity as regards the exhaust gas component to be determined and are highly resistant to poisoning. Furthermore the output signals are highly reproducible. The range of temperature in which they may be employed extends from −50° C. to 500° C.

In keeping with a preferred form of the invention the sensor in accordance with the invention is produced by a process in which the diffusion barrier consisting of porous metal is formed as a metallic paste, mixed with finely divided material such as polysterene or other propellants capable of evaporating at raised temperatures. When the metallic paste is fully fired, the added material will evaporate with the intentional production of cavities resulting in porosity. Preferably the metallic paste is applied by screen printing in this method of production. It is also an advantage if the diffusion barrier is formed by sputtering, the pore size or the channel size being dependent on the sputtering temperature and/or the level of vacuum in the sputtering chamber so that they may be adjusted by varying same. This technique is known per se.

The sensor signal is preferably processed in such a way that a signal in some form, as for example as an optical or acoustic signal, is produced when the sensor signal exceeds an adjustable and/or preset signal level. This means that if a higher concentration of the exhaust gas component, more especially the nitrogen oxide component, to be determined occurs downstream from the catalyst, an indication will be provided of the failure of the catalyst to function fully, as a result for example of a sudden contamination or of gradual aging of the catalyst. The user of the motor vehicle will so be made aware of the matter and informed that he is to replace the catalyst.

In accordance with a further, preferred form of the invention, the processing of the probe signal may be undertaken in a microprocessor, for example one forming a part of the electronic system of the vehicle and present in any case.

BRIEF DESCRIPTION OF THE DRAWINGS

The invention will now be described with reference to one working example thereof.

FIG. 1 is a diagrammatic cross sectional representation of one embodiment of the sensor taken on the section line A—A marked in FIG. 2.

FIG. 2 is a diagrammatic representation looking down onto the sensor.

DETAILED DESCRIPTION OF THE INVENTION

FIGS. 1 and 2 show a substrate 1, as for example in the form of a ceramic plate, an aluminum oxide plate or a pre-treated metal plate, on which a cathode 2 functioning as the operating electrode has been applied and, at some distance therefrom the counter electrode 3 as an anode. The operating electrode 2 consists at least in part of a porous metal, as for instance one of porous gold, acting as a diffusion barrier 7 and which has been applied to the substrate 1 in the manner noted. The exhaust gas component to be determined, as for instance a nitrogen oxide, diffuses through the operating electrode 2 acting as the diffusion barrier 7, in the vicinity of the surface of the operating electrode 2, same being in contact with a solid electrolyte 4 and being separated by an insulating layer 8 from the operating electrode 2. The electrons freed on the reduction of the nitrogen oxides make their way through the conducting electrolyte 4 to the counter electrode 3 so that the resulting current may be measured by a measuring device 6. The current signal produced on such measurement is used as an output signal when the nitrogen oxide concentration exceeds a certain level.

The entire structure is covered by an insulating guard layer 5.

For special applications it is particularly advantageous if the sensor as described is placed in the same form of arrangement on the other side of the substrate 1 in the same manner, i. e. as applied to an imaginary folded sheet so as to be symmetrical to the fold thereof. When used the one side is exposed to the gas to be determined and the other, identically formed side, is exposed to a reference gas.

The sensor in keeping with the invention may be produced in a simple, low-cost manner by a brushing or a thick layer technique. The result is then a sensor with dimensions making it suitable also for incorporation in pre-existing exhaust gas systems. Furthermore, the sensor produced in this manner is highly insensitive to vibrations.

Although the invention has only been described with reference to one working example thereof, a man versed in the art will be aware of numerous variations and developments of the invention. As an example, it is possible to incorporate a unit with the sensor as such with an integrated processing circuit—for instance one produced in hybrid technology and possibly separated by thermal insulation—so that the result is a compact integral processing component with small dimensions, which may be fitted or used as a replacement in a simple manner, as for instance to a connector formed on the exhaust gas pipe downstream from the catalyst, by means of a screw connection, whenever this is required.

We claim:

1. An electrochemical sensor for the detection of nitrogen oxides and disposable downstream of a catalyst in an exhaust pipe, the sensor comprising at least two electrodes including an operating electrode comprising a diffusion barrier integral therewith and consisting of a porous metal, a counter electrode and a solid electrolyte disposed between the operating and counter electrodes, wherein the electrolyte is a solid state electrolyte comprising spinel type or heteropolyacid compounds which are free from phase changes or decompositions within a temperature range of $-50°$ C. to $+500°$ C.

2. The sensor as claimed in claim 1, further comprising a reference electrode.

3. The sensor as claimed in claim 1, wherein the counter electrode serves as a reference electrode.

4. The sensor as claimed in claim 3, wherein the operating electrode and counter electrode consist of different materials.

5. The sensor as claimed in claim 1, wherein the operating and counter electrodes consist of the same material.

6. The sensor as claimed in claim 1, wherein the solid electrolyte consists of at least one compound which in a temperature range of $-50°$ C. to $+500°$ C. has a conductivity of at least 10-11 ohm/cm.

7. The sensor as claimed in claim 1, wherein the solid electrolyte consists of at least one compound having essentially inert behavior in relation to the electrode materials.

8. The sensor as claimed in claim 1, wherein the operating electrode consists of gold and the diffusion barrier consists of porous gold.

9. The sensor as claimed in claim 8, wherein the counter electrode consists of at least one platinum, palladium, rhodium, silver and ruthenium oxide.

10. The sensor as claimed in claim 8, wherein the counter electrode consists of silver and the reference electrode consists of $AgNO_3$.

11. The sensor as claimed in claim 8, wherein the counter electrode, consists of a mixture from the group of $Pd//PdO$, $Ni/NiO$, $Cu/Cu_2O$, $Ag/AgCl$ and $Pd/PdH_x$.

12. The sensor as claimed in claim 11, wherein the oxide mixture has a sufficiently high conductivity to produce an output signal within the nano-ampere range.

13. The sensor as claimed in claim 1, wherein the diffusion barrier consists of porous material formed by a metal paste, which is provided with finely-divided material capable of evaporating at raised temperatures and which after application to a substrate is brought to a temperature at which the added material evaporates.

14. The sensor as claimed in claim 13, wherein the metal paste is applied by screen printing.

15. The sensor as claimed in claim 13, wherein the added material is a propellant.

16. The sensor as claimed in claim 13, wherein the added material is polystyrene.

17. The sensor as claimed in the diffusion barrier is formed by sputtering.

18. The sensor as claimed in claim 17, wherein the sensor consists of two essentially identical sensor elements, one element exposed to exhaust gases and the other element exposed to a reference gas.

19. The sensor as claimed in claim 18, wherein the reference gas is external air.

* * * * *